· US009314150B2

(12) United States Patent
Chen et al.

(10) Patent No.: US 9,314,150 B2
(45) Date of Patent: Apr. 19, 2016

(54) SYSTEM AND METHOD FOR DETECTING TOOTH CRACKS VIA SURFACE CONTOUR IMAGING

(75) Inventors: Shoupu Chen, Rochester, NY (US); Rongguang Liang, Penfield, NY (US)

(73) Assignee: Carestream Health, Inc., Rochester, NY (US)

( * ) Notice: Subject to any disclaimer, the term of this patent is extended or adjusted under 35 U.S.C. 154(b) by 234 days.

(21) Appl. No.: 13/194,191

(22) Filed: Jul. 29, 2011

(65) Prior Publication Data

US 2011/0287387 A1    Nov. 24, 2011

Related U.S. Application Data

(63) Continuation-in-part of application No. 12/424,562, filed on Apr. 16, 2009.

(51) Int. Cl.
*A61C 9/00* (2006.01)
*A61B 1/247* (2006.01)
*A61B 5/00* (2006.01)
(Continued)

(52) U.S. Cl.
CPC .............. *A61B 1/247* (2013.01); *A61B 5/0088* (2013.01); *A61B 5/1077* (2013.01); *A61B 5/1079* (2013.01); *A61B 5/4547* (2013.01); *A61C 9/006* (2013.01); *G01B 11/24* (2013.01); *G01B 11/2527* (2013.01); *G03B 15/14* (2013.01); *G03B 35/08* (2013.01); *G06T 7/0014* (2013.01); *G06T 7/0057* (2013.01); *A61B 1/00009* (2013.01); *A61B 1/06* (2013.01);
(Continued)

(58) Field of Classification Search
CPC .................. A61B 5/0088; G06T 17/00–17/30; G01B 11/25–11/272; A61C 9/004–9/0066
See application file for complete search history.

(56) References Cited

U.S. PATENT DOCUMENTS 4,204,978 A    5/1980  Ibsen et al.
4,837,732 A *  6/1989  Brandestini et al. ............ 433/29
(Continued)

FOREIGN PATENT DOCUMENTS

EP    1 391 176    2/2004
EP    1 519 143    3/2005
(Continued)

OTHER PUBLICATIONS

T. Chen, H. Lensch, C. Fuchs, H. Seidel, "Polarization and Phase-Shifting for 3-D Scanning of Translucent Objects" Proceedings of IEEE Computer Society Conference on Computer Vision and Pattern Recognition (CVPR) Jun. 2007. pp. 1-8.
(Continued)

*Primary Examiner* — Serkan Akar

(57) ABSTRACT

A method for imaging the surface of a tooth, the method executed at least in part on a computer records a first set of images of the tooth, wherein each image in the first set of images is illuminated according to a pattern oriented in a first direction. A second set of images of the tooth are recorded, wherein each image in the second set of images is illuminated according to a pattern oriented in a second direction that is shifted more than 10 degrees with respect to the first direction. A first contour image is reconstructed according to the recorded first set of images and a second contour image according to the recorded second set of images. A residual image is formed as a combination of the first and second contour images. The residual image is analyzed and surface conditions of the tooth reported.

12 Claims, 17 Drawing Sheets

(51) Int. Cl.
*A61B 5/107* (2006.01)
*G01B 11/24* (2006.01)
*G01B 11/25* (2006.01)
*G03B 15/14* (2006.01)
*G03B 35/08* (2006.01)
*G06T 7/00* (2006.01)
*A61B 1/00* (2006.01)
*A61B 1/06* (2006.01)

(52) U.S. Cl.
CPC ............. *G06T2207/10016* (2013.01); *G06T 2207/20212* (2013.01); *G06T 2207/30036* (2013.01)

(56) References Cited

U.S. PATENT DOCUMENTS

| | | | |
|---|---|---|---|
| 5,372,502 | A | 12/1994 | Massen et al. |
| 5,969,754 | A | 10/1999 | Zeman |
| 6,144,453 | A | 11/2000 | Hallerman et al. |
| 6,369,899 | B1 | 4/2002 | Hamada |
| 6,584,341 | B1 | 6/2003 | Mandelis et al. |
| 6,885,464 | B1 | 4/2005 | Pfeiffer et al. |
| 7,221,420 | B2 | 5/2007 | Silverstein et al. |
| 7,312,924 | B2 | 12/2007 | Trissel |
| 7,751,871 | B2 | 7/2010 | Rubbert |
| 2002/0135752 | A1 | 9/2002 | Sokolov et al. |
| 2003/0117412 | A1 | 6/2003 | Brooksby et al. |
| 2003/0206337 | A1* | 11/2003 | Liang et al. ............ 359/352 |
| 2004/0145753 | A1 | 7/2004 | Lim et al. |
| 2004/0252312 | A1 | 12/2004 | Chen |
| 2005/0090749 | A1* | 4/2005 | Rubbert .............. 600/473 |
| 2006/0103724 | A1 | 5/2006 | Jongsma et al. |
| 2006/0132802 | A1 | 6/2006 | Chung et al. |
| 2006/0250581 | A1 | 11/2006 | Silverstein et al. |
| 2007/0015963 | A1 | 1/2007 | Fengler et al. |
| 2007/0075997 | A1* | 4/2007 | Rohaly et al. .............. 345/419 |
| 2007/0086762 | A1 | 4/2007 | O'Keefe et al. |
| 2007/0165243 | A1 | 7/2007 | Kang et al. |
| 2009/0016572 | A1* | 1/2009 | Hassebrook et al. ......... 382/106 |
| 2010/0016688 | A1 | 1/2010 | Debreczeny et al. |
| 2010/0151404 | A1* | 6/2010 | Wu et al. .................. 433/24 |

FOREIGN PATENT DOCUMENTS

| | | |
|---|---|---|
| JP | 02-119858 | 5/1990 |
| JP | 06-123610 | 5/1994 |
| JP | 10-47936 | 2/1998 |
| JP | 2005-214787 | 8/2005 |
| WO | 2009/058656 | 5/2009 |

OTHER PUBLICATIONS

C. Reich, R. Ritter, J. Thesing, "3-D shape measurement of complex objects by combining photogrammetry and fringe projection"; Opt. Eng. 39(1), Jan. 2000, pp. 224-231.

European Search Report, referring to European Patent Appln. No. 10 003 595, Jul. 2, 2010, Inventor Rongguang Liang, 2 pages.

Rudin, Osher and Fatemi, "Nonlinear Total Variation Based Noise Removal Algorithms", Physica D vol. 60, pp. 259-268, 1992.

Joachim Weickert, "Coherence-Enhancing Diffusion Filtering", International Journal of Computer Vision, vol. 31, (2/3), 1999, pp. 111-127.

Martin Fischler et al., "Analysis and Automated Cartography", Graphics and Image Processing, vol. 24, No. 6, pp. 381-395, 1981.

* cited by examiner

SYSTEM AND METHOD FOR DETECTING TOOTH CRACKS VIA SURFACE CONTOUR IMAGING

CROSS REFERENCE TO RELATED APPLICATIONS

This application is a Continuation-in-Part of commonly assigned, copending U.S. patent application Ser. No. 12/424,562 filed Apr. 16, 2009 by Liang and entitled "DENTAL SURFACE IMAGING USING POLARIZED FRINGE PROJECTION", incorporated herein by reference.

FIELD OF THE INVENTION

The invention relates generally to the field of diagnostic imaging using structured light and more particularly relates to a method for three-dimensional imaging of the surface of teeth and detection of cracks along the tooth surface using fringe projection.

BACKGROUND OF THE INVENTION

Fringe projection imaging uses patterned or structured light to obtain surface contour information for structures of various types. In fringe projection imaging, a pattern of lines of an interference fringe or grating is projected toward the surface of an object from a given direction. The projected pattern from the surface is then viewed from another direction as a contour image, taking advantage of triangulation in order to analyze surface information based on the appearance of contour lines. Phase shifting, in which the projected pattern is incrementally spatially shifted for obtaining additional measurements at the new locations, is typically applied as part of fringe projection imaging, used in order to complete the contour mapping of the surface and to increase overall resolution in the contour image.

Fringe projection imaging has been used effectively for surface contour imaging of solid, highly opaque objects and has been used for imaging the surface contours for some portions of the human body and for obtaining detailed data about skin structure. However, a number of technical obstacles have prevented effective use of fringe projection imaging of the tooth. One particular challenge with dental surface imaging relates to tooth translucency. Translucent or semi-translucent materials in general are known to be particularly troublesome for fringe projection imaging. Subsurface scattering in translucent structures can reduce the overall signal-to-noise (S/N) ratio and shift the light intensity, causing inaccurate height data. Another problem relates to high levels of reflection for various tooth surfaces. Highly reflective materials, particularly hollowed reflective structures, can effectively reduce the dynamic range of this type of imaging.

In fringe projection imaging overall, contrast is typically poor, with noise as a significant factor. To improve contrast, many fringe projection imaging systems take measures to reduce the amount of noise in the contour image. In general, for accurate surface geometry measurement using fringe imaging techniques, it is useful to obtain the light that is directly reflected from the surface of a structure under test and to reject light that is reflected from material or structures that lie beneath the surface. This is the approach that is generally recommended for 3D surface scanning of translucent objects. A similar approach must be used for intra-oral imaging.

From an optics perspective, the structure of the tooth itself presents a number of additional challenges for fringe projection imaging. As noted earlier, light penetrating beneath the surface of the tooth tends to undergo significant scattering within the translucent tooth material. Moreover, reflection from opaque features beneath the tooth surface can also occur, adding noise that degrades the sensed signal and thus further complicating the task of tooth surface analysis.

One corrective measure that has been attempted to make fringe projection workable for contour imaging of the tooth is application of a coating that changes the reflective characteristics of the tooth surface itself. Here, to compensate for problems caused by the relative translucence of the tooth, a number of conventional tooth contour imaging systems apply a paint or reflective powder to the tooth surface prior to surface contour imaging. For the purposes of fringe projection imaging, this added step enhances the opacity of the tooth and eliminates or reduces the scattered light effects noted earlier. However, there are drawbacks to this type of approach. The step of applying a coating powder or liquid adds cost and time to the tooth contour imaging process. Because the thickness of the coating layer is often non-uniform over the entire tooth surface, measurement errors readily result. Significantly, the applied coating, while it facilitates contour imaging, can tend to mask other problems with the tooth and can thus reduce the overall amount of information that can be obtained.

Even where a coating or other type of surface conditioning of the tooth is used, however, results can be disappointing due to the pronounced contours of the tooth surface. It can be difficult to provide sufficient amounts of light onto, and sense light reflected back from, all of the tooth surfaces. The different surfaces of the tooth can be oriented at 90 degrees relative to each other, making it difficult to direct enough light for accurately imaging all parts of the tooth.

There have been a number of attempts to adapt structured light surface-profiling techniques to the problems of tooth structure imaging. For example, U.S. Pat. No. 5,372,502 entitled "Optical Probe and Method for the Three-Dimensional Surveying of Teeth" to Massen et al. describes the use of an LCD matrix to form patterns of stripes for projection onto the tooth surface. A similar approach is described in U.S. Patent Application Publication 2007/0086762 entitled "Front End for 3-D Imaging Camera" by O'Keefe et al. U.S. Pat. No. 7,312,924 entitled "Polarizing Multiplexer and Methods for Intra-Oral Scanning" to Trissel describes a method for profiling the tooth surface using triangularization and polarized light, but needing application of a fluorescent coating for operation. Similarly, U.S. Pat. No. 6,885,464 entitled "3-D Camera for Recording Surface Structures, In Particular for Dental Purposes" to Pfeiffer et al. discloses a dental imaging apparatus using triangularization but also requiring the application of an opaque powder to the tooth surface for imaging.

It is known that cracks or fractures in teeth can be difficult to detect, whether using visible light or x-ray imaging. U.S. Pat. No. 4,204,978 to Ibsen et al. discloses tooth crack detection using a composition or solution for detecting the location of normally invisible cracks in a tooth. Such methods require a number of chemicals and require operator training; further, the materials used can stain the tooth. U.S. Pat. No. 6,584,341 to Mandelis et al. describes a photothermal radiometric and luminescence method for locating cracks along the enamel surface. The method in '341 irradiates a portion of a surface of a tooth at an effective wavelength. Both photothermal radiometric signals and luminescence signals are then emitted from the portion of the tooth that has been irradiated. The photothermal radiometric signals and luminescence signals are detected and demodulated into phase and amplitude components. The demodulated phase and amplitude components are compared to luminescence phase and amplitude signals of a reference sample to determine differences between the portion of the tooth and the reference sample. This type of method is fairly costly and complex, making it impractical for widespread use.

It can be appreciated that there would be benefits to a low-cost apparatus and method that not only provides accurate surface contour imaging of the tooth, without the need for applying an added coating or other conditioning of the tooth surface for this purpose, but also provides crack detection without other equipment or light source.

SUMMARY OF THE INVENTION

It is an object of the present invention to advance the art of medical imaging, particularly for intra-oral imaging applications, with particular interest in detection of cracks and other surface features of the tooth.

It is a feature of the present invention that it applies light of suitable polarization and wavelength along with fringe projection patterning of varying brightness to the task of tooth contour imaging. Both the surface contour imaging and crack imaging are performed with the same intraoral apparatus so that surface contour image and crack image can be easily registered and visualized, which can help to speed reconstructive dentistry and to lower the inherent costs and inconvenience of conventional methods, such as those for obtaining a cast or other surface profile for a crown, implant, or other restorative structure.

An advantage offered by the apparatus and method of the present invention relates to improved imaging of tooth surfaces and at lower cost over conventional contour imaging methods. Unlike conventional methods, no powder or other opaque substance must be applied to the tooth as a preparatory step for contour imaging or crack detection.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present invention, there is provided a method for imaging the surface of a tooth, the method executed at least in part on a computer and comprising: recording a first set of images of the tooth, wherein each image in the first set of images is illuminated according to a pattern oriented in a first direction; recording a second set of images of the tooth, wherein each image in the second set of images is illuminated according to a pattern oriented in a second direction that is shifted more than 10 degrees with respect to the first direction; reconstructing a first contour image according to the recorded first set of images and a second contour image according to the recorded second set of images; forming a residual image as a combination of the first and second contour images; and analyzing the residual image and reporting surface conditions of the tooth.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
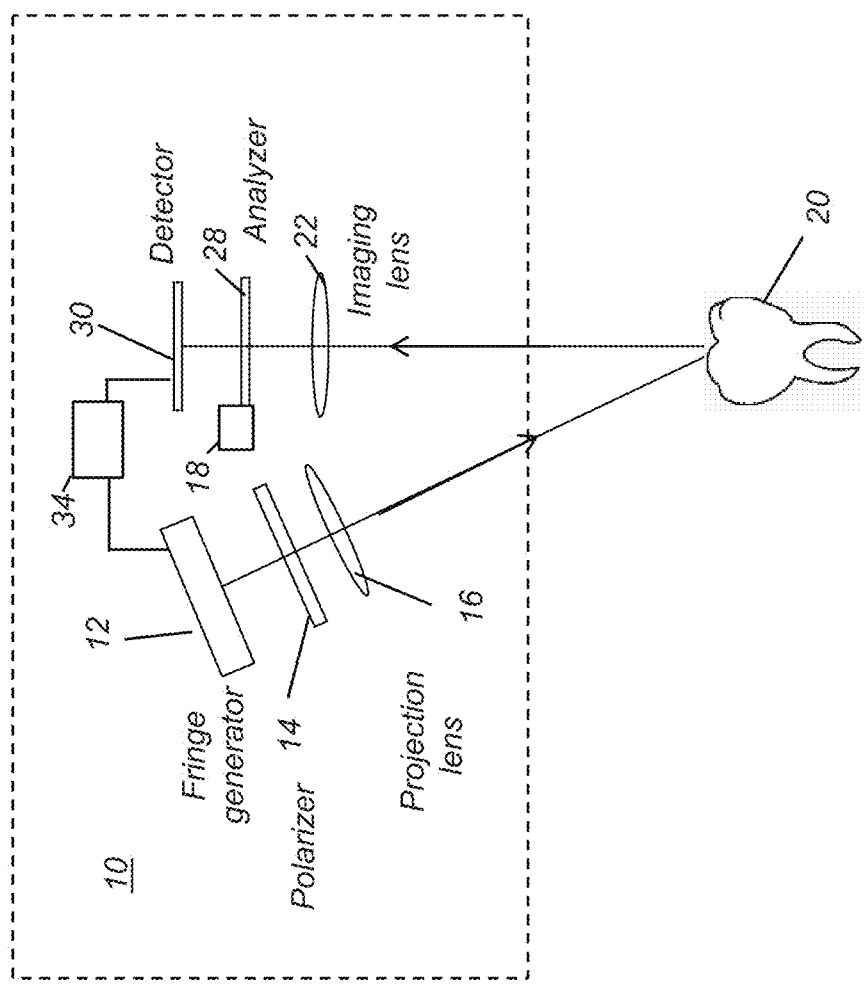
FIG. 1 is a schematic diagram of an imaging apparatus using polarized fringe projection imaging in one embodiment.

Figures provided herein are given in order to illustrate key principles of operation and component relationships along their respective optical paths according to the present invention and are not drawn with intent to show actual size or scale. Some exaggeration may be necessary in order to emphasize basic structural relationships or principles of operation. Some conventional components that would be needed for implementation of the described embodiments, such as support components used for packaging and for mounting and protecting system optics, for example, are not shown in the drawings in order to simplify description of the invention itself. In the drawings and text that follow, like components are designated with like reference numerals, and similar descriptions concerning components and arrangement or interaction of components already described are omitted.

In the context of the present disclosure, the term "fringe pattern illumination" is used to describe the type of structured illumination that is used for fringe projection imaging or "contour" imaging. The fringe pattern itself can include, as pattern features, multiple lines, circles, curves, or other geometric shapes that are distributed over the area that is illuminated and have a predetermined spatial frequency, recurring at a given period.

In the context of the present disclosure, the term "crack" refers to a crack, cleft, or other fissure that denotes a crack or fracture along at least some portion of the tooth surface.

Two portions of a line of light or other feature in a pattern of structured illumination can be considered to be substantially "dimensionally uniform" when their line width is the same over the length of the line to within no more than +/−15 percent. As is described in more detail subsequently, dimensional uniformity of the pattern of structured illumination is needed to maintain a uniform spatial frequency.

As noted earlier in the background section, conventional approaches for fringe projection imaging fall short of providing good results for tooth tissue for a number of reasons. Apparatus and methods of the present invention address the problems of obtaining images of the tooth when using fringe projection imaging with fringe pattern illumination by selection of favorable light properties and by techniques that improve light delivery to the highly contoured tooth surface.

Referring to the schematic block diagram of FIG. 1, there is shown an embodiment of an intra-oral imaging apparatus 10 for obtaining surface contour information from a tooth 20 using structured light. A fringe pattern generator 12 is energizable to form the structured light as a fringe pattern illumination and project the structured light thus formed as incident light toward tooth 20 through a polarizer 14 and projection lens 16. Light reflected and scattered from tooth 20 is provided to a detector 30, through an imaging lens 22 and an analyzer 28. Detector 30 is disposed along the detection path, at the image plane of imaging lens 22. A control logic processor 34 accepts feedback information from detector 30 and, in response to this and other data, is actuable to effect the operation of pattern generator 12, as described in more detail subsequently.

One function of control logic processor 34 for fringe projection imaging is to incrementally shift the position of the fringe and trigger the detector to take images that are then used to calculate three-dimensional information of tooth surface. For the phase shifting fringe projection method, at least three images are typically needed in order to provide enough information for calculating the three-dimensional information of the object. The relative positions of the fringes for these three projected images are shifted by one-third of the fringe period. Control logic processor 34 can be a computer, microprocessor, or other dedicated logic processing apparatus that executes programmed instructions obtained from a computer accessible memory.

Another function of control logic processor 34 for fringe projection is to rotate the fringe. This function can be of particular value for detecting tooth cracks or fractures, as described in more detail subsequently.

Figure 2A:
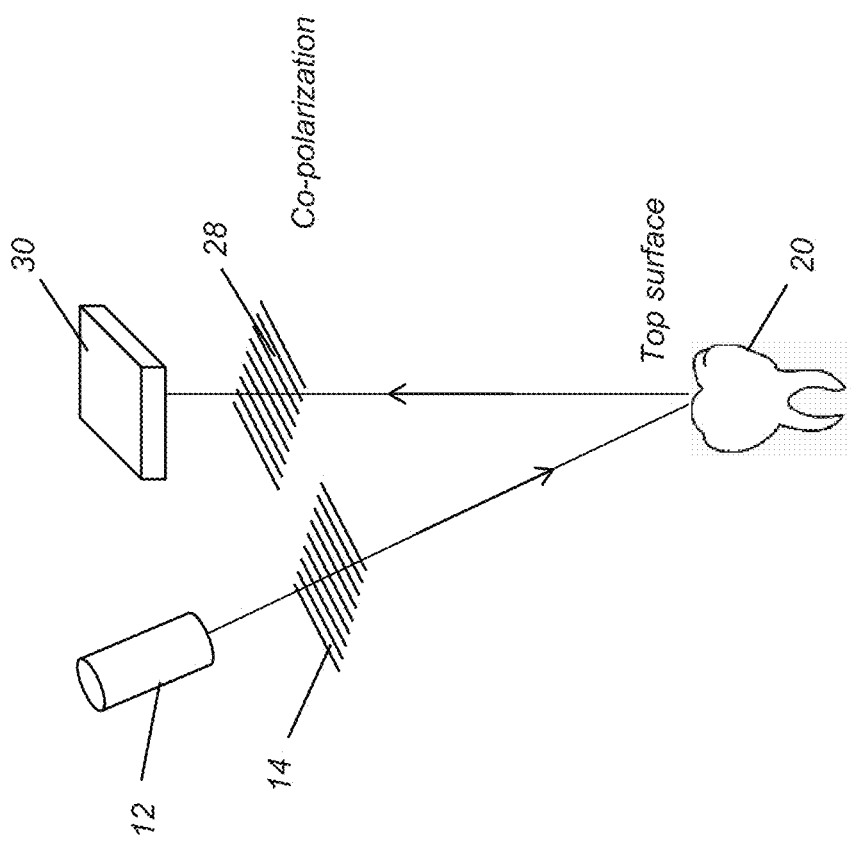
FIG. 2A is a block diagram showing the use of an analyzer with its polarization axis in parallel to the polarizer of a polarized fringe projection imaging apparatus.

Intra-oral imaging apparatus 10 of FIG. 1 uses polarized light for surface imaging of tooth 20. Polarizer 14 provides the fringe pattern illumination from fringe pattern generator 12 as linearly polarized light. In one embodiment, the transmission axis of analyzer 28 is parallel to the transmission axis of polarizer 14. With this arrangement, only light with the same polarization as the fringe pattern is provided to the detector 30. In another embodiment, analyzer 28, in the path of reflected light to detector 30, is rotated by an actuator 18 into either of two orientations as needed:

(i) Same polarization transmission axis as polarizer 14. In this "co-polarization" position, detector 30 obtains the specular light reflected from the surface of tooth 20, and most of the light scattered and reflected from the superficial layer of enamel surface of tooth 20, as well as some of the light scattered back from sub-surface portions of the tooth. The co-polarization orientation of the analyzer 28 axis is shown in FIG. 2A. Parallel or co-polarization provides improved contrast over other configurations.

Figure 2B:
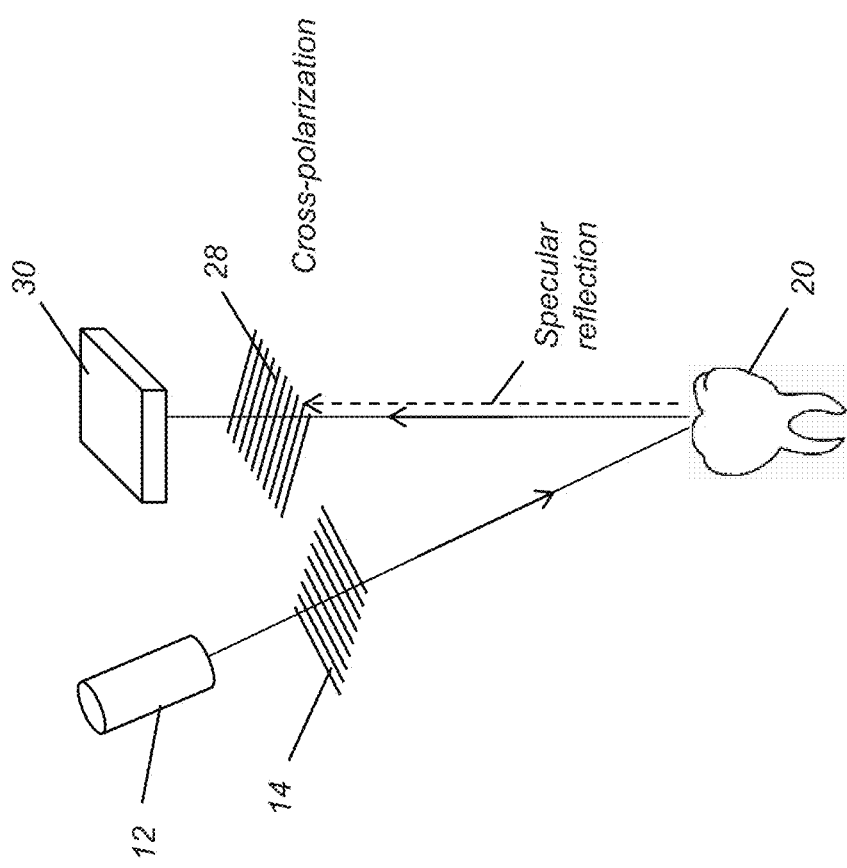
FIG. 2B is a block diagram showing the use of an analyzer with its polarization axis orthogonal to the polarizer of a polarized fringe projection imaging apparatus.

(ii) Orthogonal polarization transmission axis relative to polarizer 14. Using the orthogonal polarization, or cross-polarization, helps to reduce the specular component from the tooth surface and obtain more of the scattered light from inner portions of the tooth. The cross-polarization orientation of the analyzer 28 axis is shown in FIG. 2B.

When the tooth is imaged with an imaging system and sensor, the light that is available to the sensor can be (i) light reflected from the tooth top surface; (ii) light scattered or reflected from the near surface volume or portion of the tooth; and (iii) light scattered inside the tooth. In the context of the present disclosure, the "near-surface volume" of the tooth is that portion of the tooth structure that lies within no more than a few hundred μm of the surface.

It is known that the light reflected from the tooth surface (i), the specular light, maintains the polarization state of the incident light. As the incident light propagates further into the tooth, the light is increasingly depolarized.

Disadvantageously, some portion of the specular light (i) for a contour pattern may be incident on more highly reflective portions of the tooth surface, even causing some amount of saturation that degrades light detection. In contrast to conventional approaches that use all the light from the tooth, methods of the invention use at least portions of both the specular light (i) and the near-surface reflected light (ii), and avoid the light scattered deep inside the tooth (iii). The inventors have found that the near-surface light (ii), particularly for blue light and shorter wavelengths, is still substantially polarized. Thus, for example, a large portion of the light scattered and reflected from the superficial layer of the tooth enamel also has the same polarization state as the incident light and as the specular light (i).

Figure 3B:
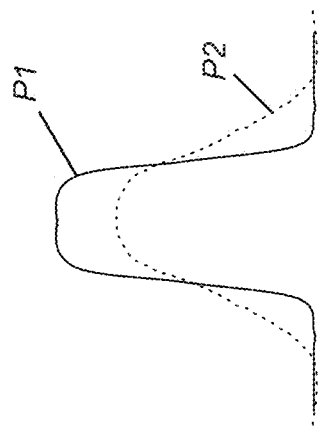
FIG. 3B is a diagram showing the relative intensities of reflected light and the scattered light from incident illumination.
Figure 3A:
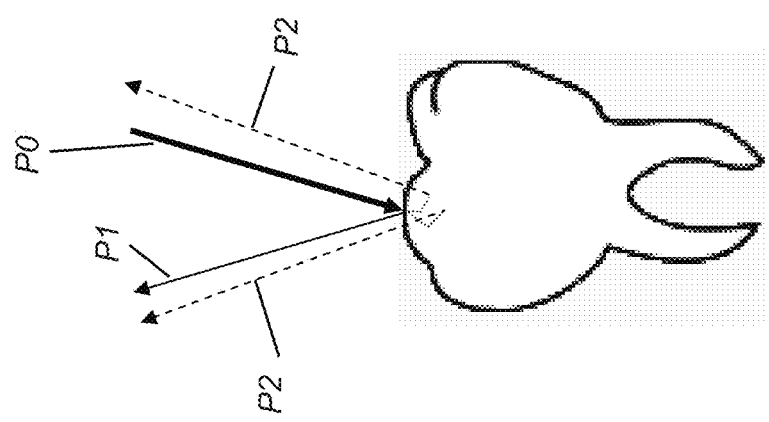
FIG. 3A shows the polarization-dependent reflection and scattering of illumination incident on the tooth.

FIG. 3A shows why the apparatus and method of the present invention use scattered near-surface light from just beneath the surface of the tooth. When a polarized light P0 with small beam dimension illuminates the tooth, some of the light P1 is reflected from the surface of the tooth in specular fashion and has the same polarization state as the illumination light P0. The other portion of the illumination light P0 goes into the tooth, is subject to scattering and depolarizes. Some of the scattered light P2 escapes the tooth surface near the illumination region and can reach detector 30 (FIG. 1).

Significantly, the spatial "footprint" of the scattered light P2, which relates to the dimensions of pattern features of the structured light, such as line thicknesses, shows an increase over the corresponding spatial footprint of reflected light P1. For example, where the structured light pattern consists of parallel lines of light of a given thickness, the reflected light P1 from these pattern features has lines of the same thickness as the projected pattern. However, the scattered light P2 is detected as lines of slightly increased thickness. That is, since light P2 has been scattered inside the tooth, the projected footprint on the tooth surface is broader than that of the specular reflected light, which is the same size as the illumination beam. The graph of FIG. 3B shows the difference between the footprint of the light from the tooth surface and that from inside the tooth. To reduce the measurement error that can result, the light detected from inside the tooth should be minimized. The inventors have found that polarization provides an effective discriminator for separating the specular light (P1) from the tooth surface from the scattered light from inside the tooth, while still taking advantage of a portion of the scattered light (P2).

Figure 4C:
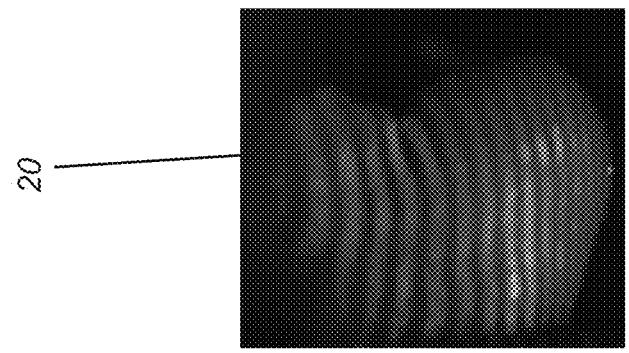
FIGS. 4A, 4B, and 4C are perspective views of a tooth imaged with fringe projection imaging, using non-polarized light, cross-polarized light, and co-polarized light, respectively.
Figure 4B:
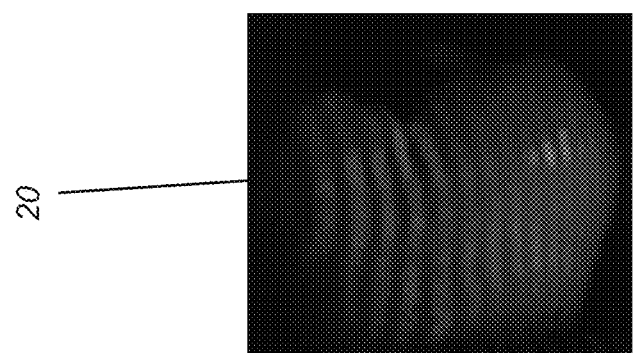
Figure 4A:
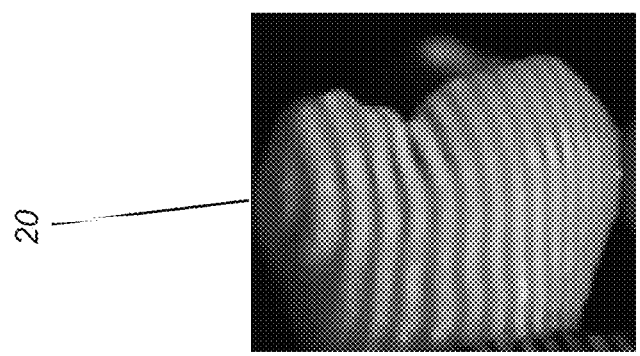

The group of contour images shown in FIGS. 4A-4C give a comparison of approaches for obtaining and using light returned from the tooth using fringe projection. FIG. 4A shows a contour image of tooth 20 obtained using unpolarized light. FIG. 4B shows a somewhat poorer image using cross-polarized light, but not exhibiting specular reflection. FIG. 4C shows the improvement in the image contrast when using co-polarized light. Areas of high brightness in this image are due to specular reflection. As these images show, fringe contrast improves when the cross-polarization light is blocked from the image detector.

Figure 5A:
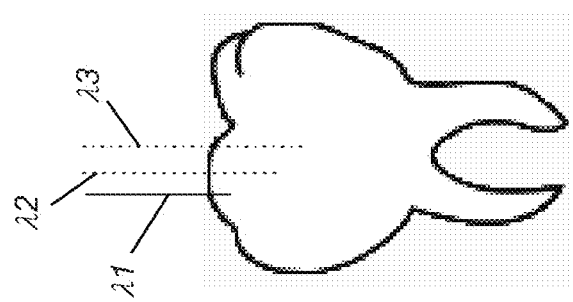
FIG. 5A is a diagram showing wavelength-dependent penetration of illumination incident on the tooth.
Figure 5B:
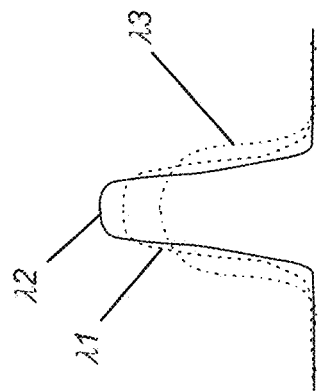
FIG. 5B is a schematic diagram showing relative intensities of reflected and scattered light with different wavelengths.

In addition to taking advantage of favorable properties of polarized light, embodiments of the present invention also take advantage of different amounts of reflection that correspond to the wavelength of light directed toward the tooth. FIG. 5A shows three different wavelengths $\lambda 1$, $\lambda 2$, and $\lambda 3$ as directed toward tooth 20. The shortest wavelength at $\lambda 1$ penetrates the tooth the shortest distance. The next longest wavelength at $\lambda 2$ penetrates the tooth an additional distance. Finally, the longest wavelength at $\lambda 3$ penetrates the tooth the farthest distance. The graph of FIG. 5B shows how scattering affects the footprint of the light on the tooth surface from each wavelength. The longer the wavelength, the larger the footprint, resulting in larger measurement error. Wavelength $\lambda 1$ could be near-UV or blue light in the range of 350 to 500 nm, for example. Wavelength $\lambda 2$ could be green light in the range of 500 to 700 nm, for example. Wavelength $\lambda 3$ could be red or IR light in the range of 700 nm or higher, for example. Thus, blue or near UV light in the 350-500 nm range, because it provides the least penetration into the tooth structure, proves to be a suitable light source for fringe projection imaging in one embodiment.

For the embodiment of FIG. 1, light modulators can be used as part of fringe pattern generator 12 to provide the needed shifting motion for polarized fringe projection imaging, as described in more detail subsequently. The fringe pattern itself is shifted to at least one alternate position during imaging. This shifting of the light pattern can be caused by a separate actuator (not shown in FIG. 1), such as a piezoelectric or other type of actuator that is part of fringe pattern generator 12 for achieving precision incremental movement. Alternately, fringe pattern generator 12 can use a spatial light modulator to do this shifting electronically, without mechanical movement of parts within fringe pattern generator 12. In addition, another actuator 18 can be positioned for providing 90 degree rotation to either polarizer 14 or analyzer 28 (such as is shown in FIG. 1) in order to obtain both co-polarization and cross-polarization images. Polarization can also be rotated when using an LCD spatial light modulator.

Figure 6:
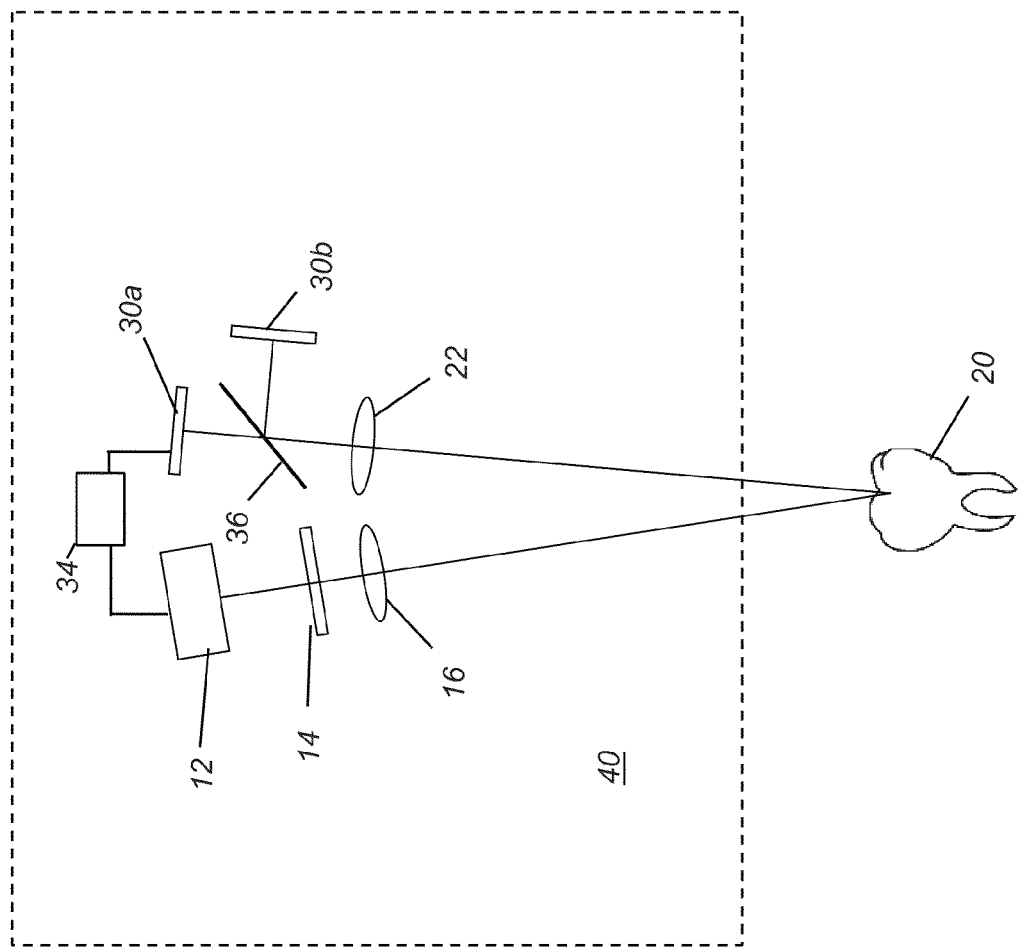
FIG. 6 is a schematic diagram showing an imaging apparatus for obtaining both co-polarized and cross-polarized light in fringe projection imaging.

FIG. 6 shows an embodiment of an intra-oral imaging apparatus 40 that obtains images using both parallel and cross-polarization without requiring rotation of either polarizer 14 or analyzer 28 between image captures. A polarization beam splitter 36 separates the reflected and scattered light, reflecting the cross-polarized light to a detector 30b and transmitting the co-polarized light to a detector 30a.

Because the co-polarized and cross-polarized light provide different types of information about the surface and near-surface of the tooth, imaging apparatus 40 of FIG. 6 offers the advantage of using both polarizations without the need for mechanical movement of analyzer 28 or polarizer 14, combining the results from orthogonal polarizations in order to obtain improved surface contour data.

Detectors 30, 30a, or 30b in the embodiments described herein can be any of a number of types of image sensing array, such as a CCD device, for example. Polarizers and analyzers can be wire-grid or other polarizer types.

Figure 7:
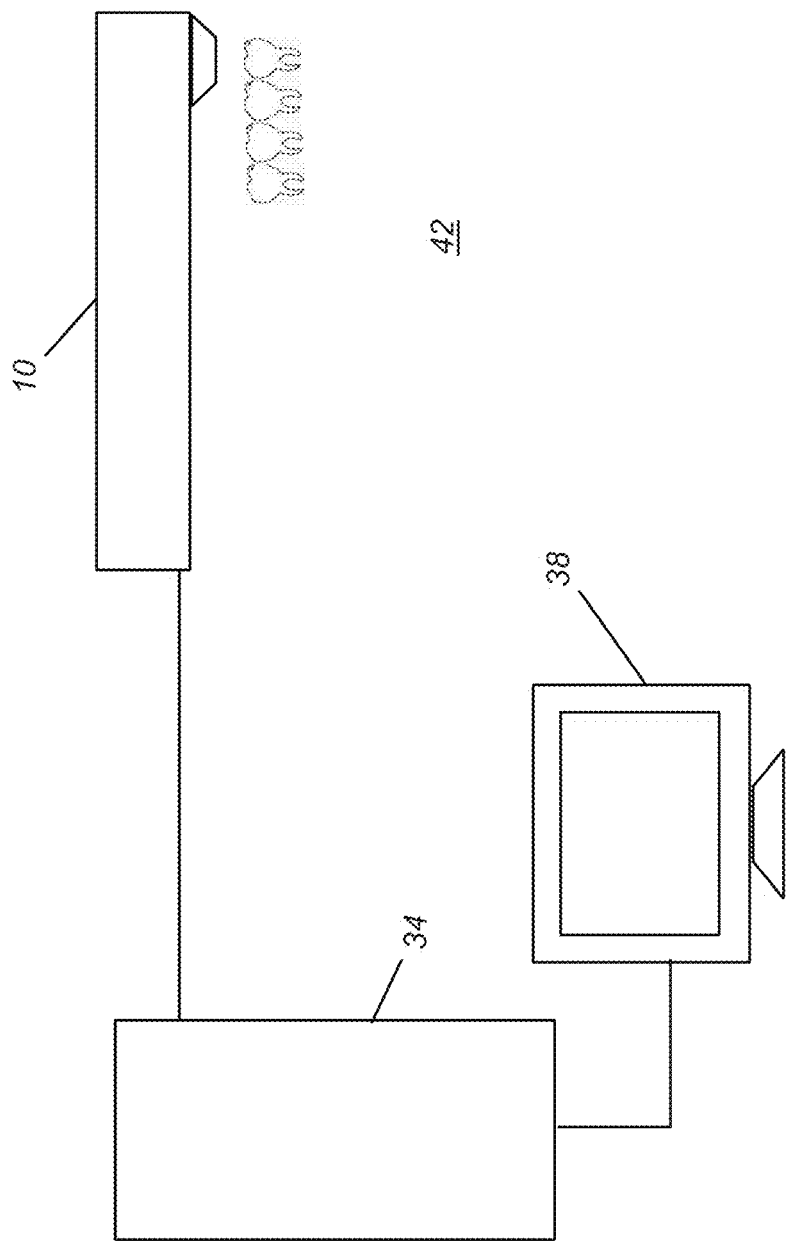
FIG. 7 is a block diagram showing components of an intraoral imaging system according to one embodiment.

In one embodiment of the present invention, the imaging apparatus is packaged in the form of a hand-held probe that can be easily positioned within the patient's mouth with little or no discomfort. Referring to FIG. 7, there is shown an intra-oral imaging system 42 that includes imaging apparatus 10 in the form of a probe. The probe communicates, over a wired or wireless data communication channel, with control logic processor 34 that obtains the images from either or both co-polarized and cross-polarized projection fringes. Control logic processor 34 provides output image data that can be stored as a data file and displayed on a display 38.

Figure 8:
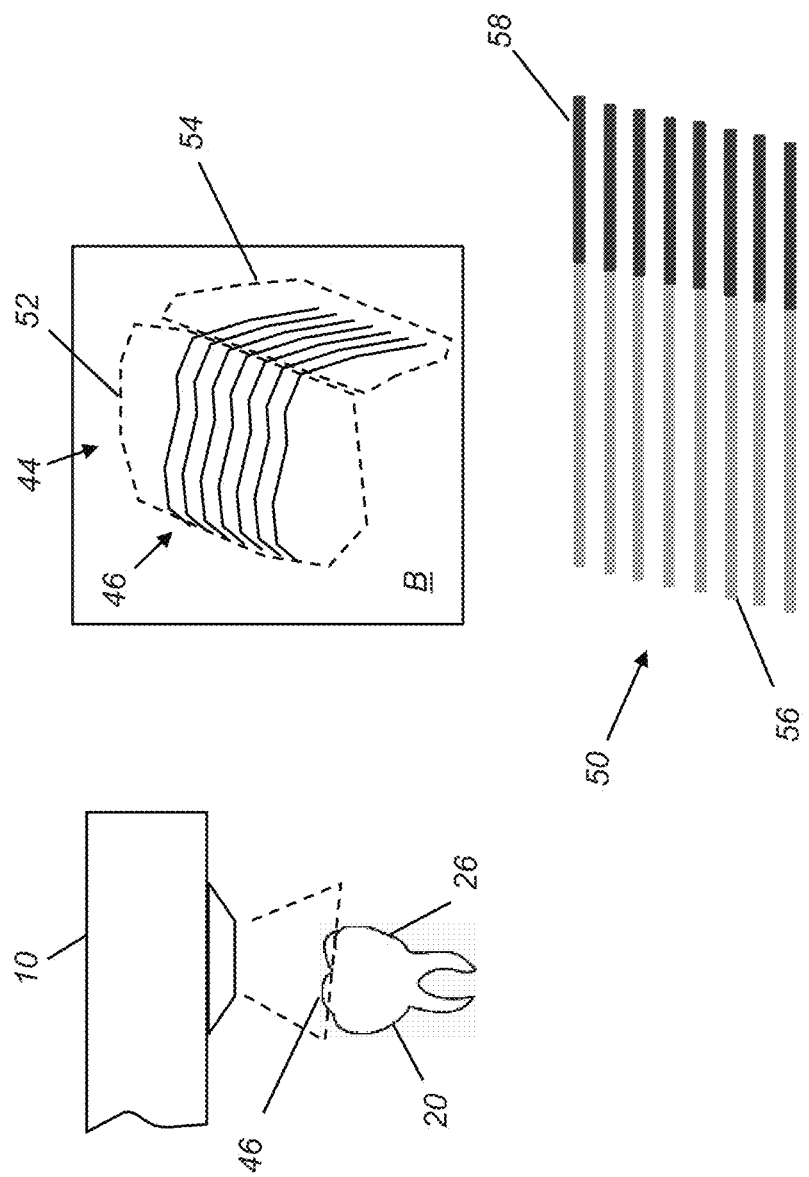
FIG. 8 is a schematic diagram showing how increased brightness can be applied for improved imaging over a portion of the imaging field with contoured surfaces.

As was noted in the background material given earlier, the pronounced contours of the tooth include surfaces that are steeply sloped with respect to each other, complicating the task of directing enough light onto each surface. As a result, some surfaces of the tooth may not provide 3-D information that is sufficient. Referring to FIG. 8, this problem is represented relative to a rear surface 26 of tooth 20. Patterned light from imaging apparatus 10 generates a contour-detecting fringe pattern 44 onto tooth 20, as shown in box B. Fringe pattern 44 is sufficiently bright for obtaining 3-D image content over a top surface area 46, as outlined over an area 52; however, the back surface area corresponding to rear surface 26 of tooth 20 and outlined as a darker area 54 is very dimly lit. This allows only a coarse estimation, at best, of the contour of rear surface 26.

In order to compensate for this lack of brightness using conventional fringe projection patterning techniques, an embodiment of the present invention selectively increases the light intensity of the fringe pattern illumination over a given area. In FIG. 8, a fringe pattern 50 is shown with two different areas, differentiated by their relative light intensities. In fringe pattern 50, a first intensity 56 is provided for fringe projection imaging of surfaces such as top surface area 46 that are more readily accessible for contour imaging. A second intensity 58, higher than first intensity 56 for the example shown and as indicated by darker lines in FIG. 8, is provided for the back surface area of the tooth. It should be observed that the actual pattern feature spacing and thickness of the projected contour lines that are the pattern features in this example is not changed in this embodiment. The same spatial frequency of fringe pattern 50 is preserved. This means that the contour pattern, fringe pattern 50, remains dimensionally uniform, with individual lines or other pattern features changed only in intensity, rather than in dimension or spacing (period). Only the relative intensity of the fringe pattern illumination over one or more areas is increased where needed. For example, along any one line within structured light fringe pattern 50, there can be any number of intensities, such as the two shown as first and second intensities 56 and 58 in FIG. 8. The line thickness within the fringe pattern does not change.

Maintaining dimensional uniformity and spatial frequency of the fringe pattern is advantageous for contour imaging because it provides a uniform resolution over the full image field. Other techniques have been proposed for changing the pattern dimensions itself, such as thickening the pattern lines over specific areas; however, using such a technique, because the spatial frequency of the fringe pattern changes, the resulting resolution is non-uniform. With respect to the example fringe pattern 50 given in FIG. 8, it is instructive to observe that if the area indicated as second intensity 58 actually used thicker lines, the resulting contour image would suffer reduced resolution over this area. By maintaining the lines of fringe pattern 50 as dimensionally uniform and only increasing the intensity of light to provide second intensity 58 in this example, embodiments of the present invention provide an increased illumination without loss of resolution over the darker region.

Figure 9B:
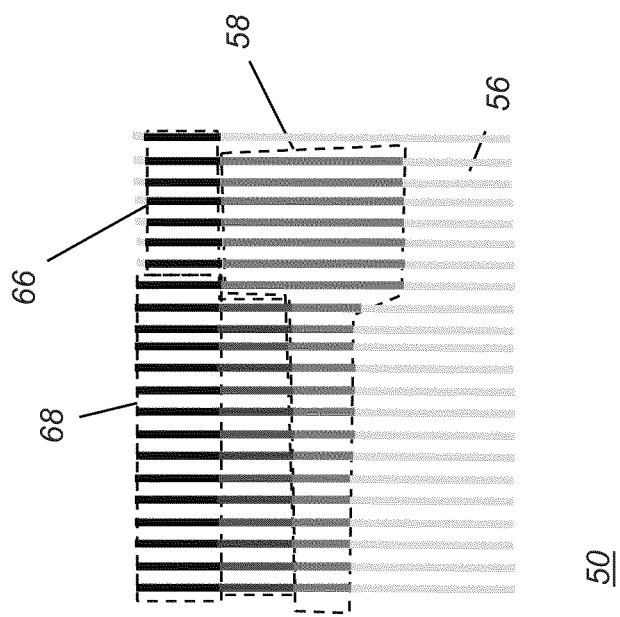
FIGS. 9A and 9B show exemplary projected light patterns generated for contour imaging in one embodiment.
Figure 9A:
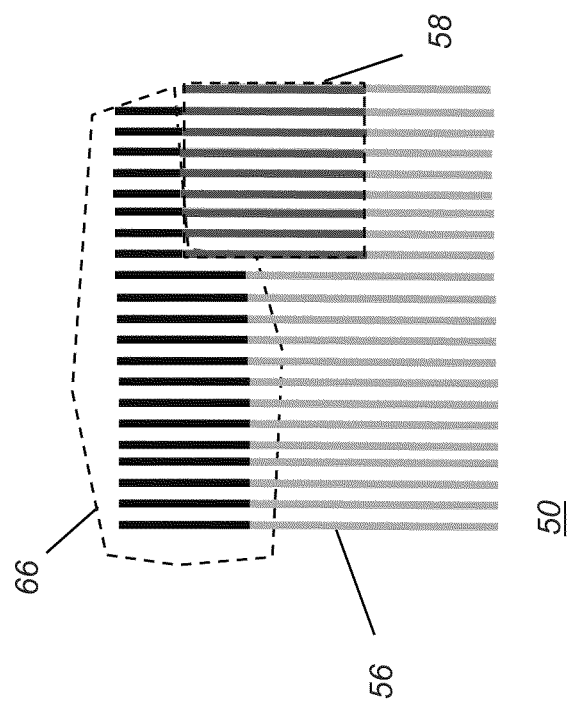

The schematic diagram of FIG. 8 showed a simple case in which fringe pattern 50 compensates for surface steepness by using two different intensities 56 and 58. FIGS. 9A and 9B show examples of other possible arrangements that use more than two light intensities. In FIG. 9A, for example, light for the fringe pattern illumination can be of first intensity 56, second intensity 58, or a third intensity 66, represented as the highest intensity in this example. In FIG. 9B, light can be of first, second, or third intensities 56, 58, or 66 respectively, or of an even higher fourth intensity 68 as shown. The light intensity can vary along any individual pattern feature, such as along a single line in the projected fringe pattern 50.

In addition to increasing the light intensity over darker areas of the tooth surface relative to the position of imaging apparatus 10, it is also possible to reduce the light intensity over areas where there may be highly specular reflection, resulting in saturation of the detector. Again, it must be emphasized that what changes is the light intensity over one or more portions of the projected light pattern; line thickness and spacing, both related to the spatial frequency, remain the same for different intensities.

Referring back to the block diagrams of FIG. 1 or 6, the light intensity over the projected pattern can be changed by controlling fringe pattern generator 12 by means of commands from control logic processor 34, in response to programmed instructions, and by means of signals provided from control logic processor 34 to related control components. In one embodiment, fringe pattern generator 12 is a digital micromirror device (DMD). Intensity can then be increased over any portion of projected fringe pattern 50 by increasing the effective duty cycle of the rotatable mirrors using Pulse-Width Modulation (PWM), so that the source illumination is provided for a suitable amount of time over a particular portion of the fringe pattern. Other methods of illumination intensity adjustment would apply for LCD and emissive spatial light modulators, using light modulation techniques familiar to those skilled in the imaging arts.

Figure 10:
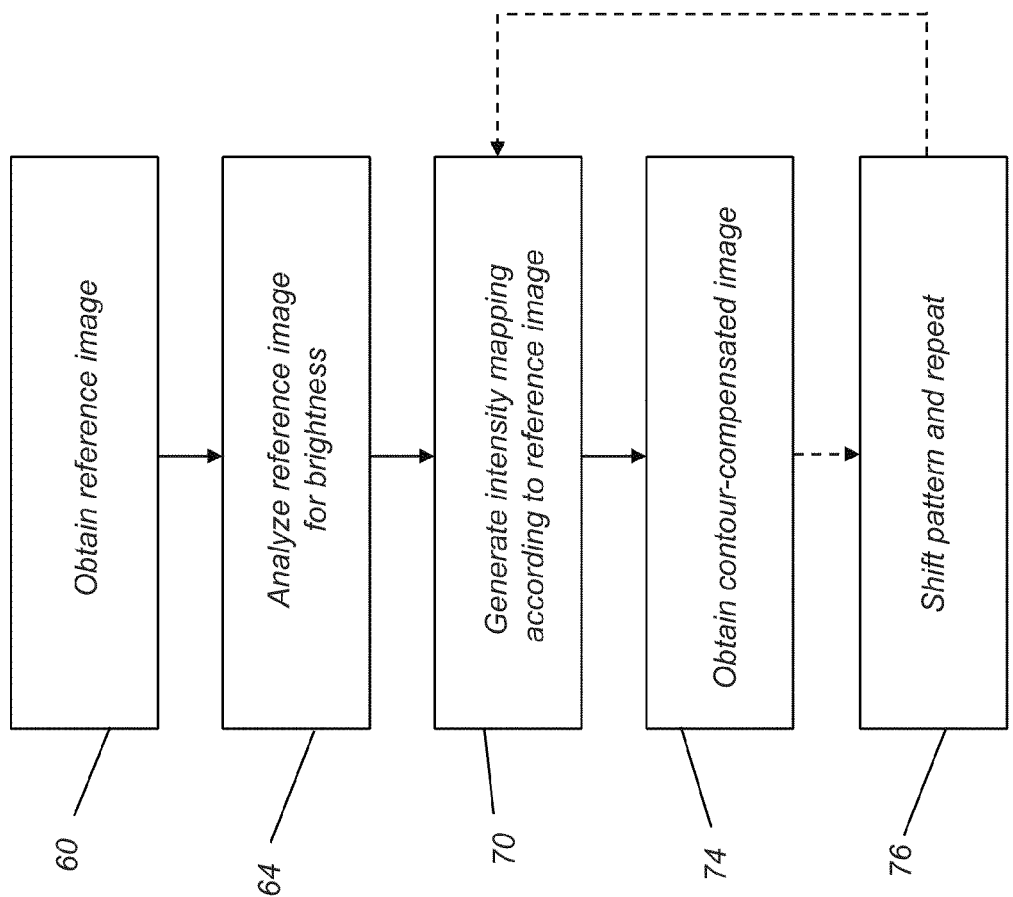
FIG. 10 is a logic flow diagram that shows the sequence for obtaining a contour-compensated image.

Referring back to FIG. 7, control logic processor 34 is programmed with instructions that automatically adapt the local intensities of lines or other features in fringe pattern 50 according to imaging conditions. The logic flow diagram of FIG. 10 shows a sequence of steps that are used for adaptive fringe projection imaging in one embodiment. In an initial step 60 a first reference image is obtained. The reference image can be a contour image, formed by projecting structured light onto the tooth surface. Alternately, the reference image can be a conventional two-dimensional image obtained from projection of a uniform field of light onto the tooth surface. The reference image that is obtained can be at full resolution; alternately, since the reference image is not used directly for imaging but instead to determine the overall amount of light that is returned, the reference image can be at lower resolution.

Still referring to FIG. 10, an analysis step 64 follows, in which areas from the sensed reference image that are not sufficiently bright are identified. For dental imaging applications, analysis step 64 can take advantage of known data about tooth structure. The operator, for example, may identify the tooth by number or provide other information that is used in analysis step 64. A map generation step 70 is then executed, in which areas of greater or lesser intensity are defined according to the first reference image. With respect to FIGS. 9A and 9B, step 70 then sets up variable intensity fringe pattern 50. An image acquisition step 74 then uses the generated fringe pattern 50 for obtaining a contour image with added brightness as described with respect to FIG. 8. Image acquisition step 74 may be followed by an optional looping step 76 that repeats the analysis of map generation step 70 in order to generate a second or other additional mappings so that the projected structured illumination pattern can be shifted, with appropriate changes in intensity, one or more times in order to obtain a more accurate evaluation of tooth contour using fringe projection techniques, then combining the individually obtained contour images to obtain surface structure information, using techniques well known in the imaging arts. In one embodiment, image acquisition step 74 also includes energizing actuator 18 (FIG. 1) in order to obtain images using both co-polarization (as in FIG. 2A) and cross-polarization (FIG. 2B).

Figure 11:
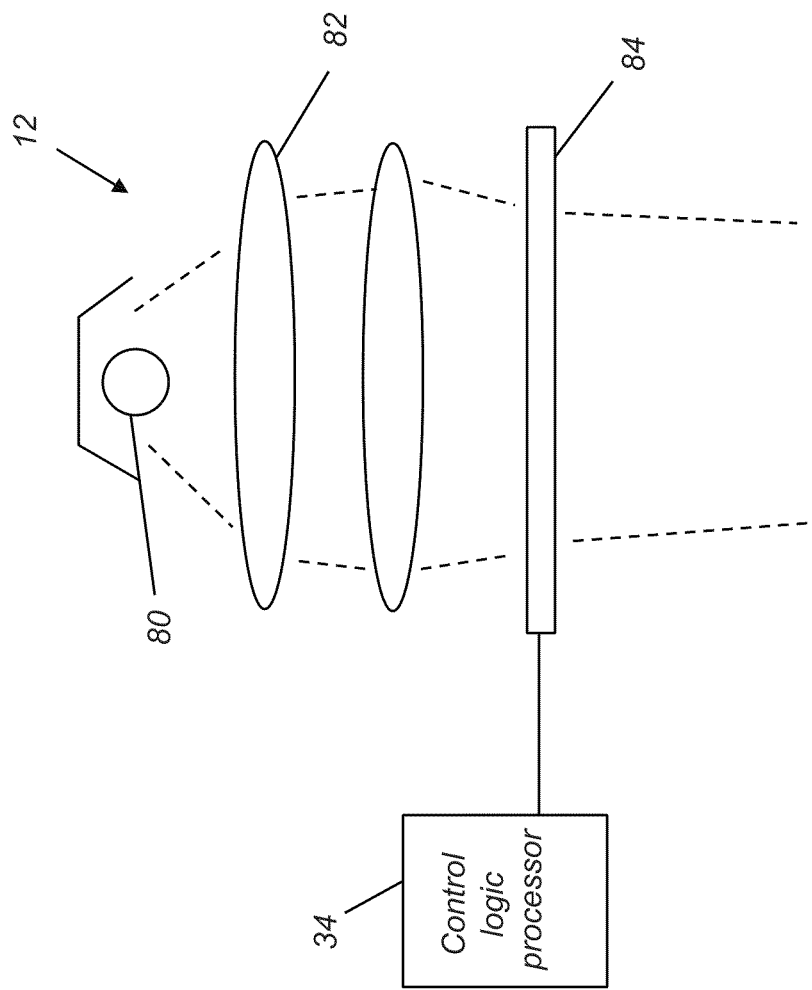
FIG. 11 is a schematic block diagram showing components of a pattern generator in one embodiment.

FIG. 11 is a schematic block diagram showing components of fringe pattern generator 12 in one embodiment. A spatial light modulator 84, such as a digital micromirror device (DMD), liquid crystal device (LCD), or other type of light modulator array or grating forms a pattern according to control signals from control logic processor 34. A light source 80 provides incident light to spatial light modulator 84, conditioned by one or more optical elements 82, such as a light uniformizer and lens elements. Spatial light modulator 84 may be a transmissive device as shown in FIG. 11 or a reflective device, such as a DMD. Control logic processor 34 responds to pattern 44 of light brightness that is returned in the initial reference image as was described earlier with reference to FIG. 8 to control the intensity of pattern features in the fringe pattern that it forms on spatial light modulator 84.

In the embodiment of FIG. 11, light source 80 can be a solid-state light source, such as a Light-Emitting Diode (LED) or laser, or can be a lamp or other light source. Blue or near UV light in the 350-500 nm range is used for providing usable image content from near-surface portions of the tooth, as described earlier. In an alternate embodiment, light source 80 is not used and an emissive array, such as an Organic LED (OLED) is used for pattern generation from a single component.

Figure 12:
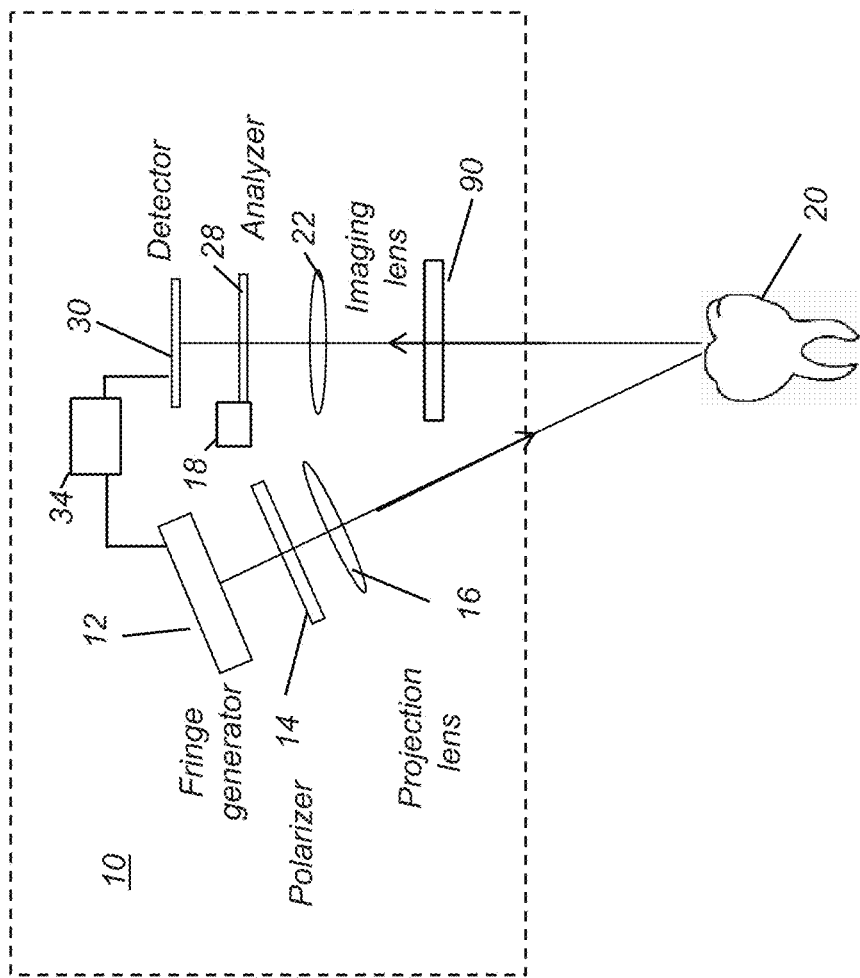
FIG. 12 is a schematic diagram of an imaging apparatus using polarized fringe projection imaging in one embodiment.

The schematic diagram of FIG. 12 shows another embodiment of the present invention wherein a filter 90, such as a bandpass filter that transmits blue or near UV light in the 350-500 nm range and attenuates other light, is placed in the imaging path. This embodiment can be less sensitive to factors in the environment, such as stray light from other equipment in the room. In this embodiment, light source 80 within fringe pattern generator 12 (FIG. 11) can be either broadband, extending well beyond the 350-500 nm range, or narrowband, primarily emitting blue and near-UV light.

Embodiments of the present invention provide improved contour imaging for teeth by taking advantage of properties of light and capabilities of spatial light modulators for forming an adaptive fringe projection pattern having suitable light intensity that is responsive to variability in tooth surface characteristics. The apparatus and methods of the present invention compensate for problems related to the translucence of the tooth by using short-wavelength light and by employing principles of polarized light. When light of suitable wavelength and polarization state is provided with an adaptable intensity arrangement, a more accurate indicator of the highly contoured tooth surface can be achieved.

The surface contour image that is obtained using the apparatus and methods of the present invention can be used in a number of ways. Contour data can be input into a system for processing and generating a restorative structure or can be used to verify the work of a lab technician or other fabricator of a dental appliance. This method can be used as part of a system or procedure that reduces or eliminates the need for obtaining impressions under some conditions, reducing the overall expense of dental care. Thus, the imaging performed using this method and apparatus can help to achieve superior fitting prosthetic devices that need little or no adjustment or fitting by the dentist. From another aspect, the apparatus and method of the present invention can be used for long-term tracking of tooth, support structure, and bite conditions, helping to diagnose and prevent more serious health problems. Overall, the data generated using this system can be used to help improve communication between patient and dentist and between the dentist, staff, and lab facilities.

Advantageously, the apparatus and method of the present invention provide an intra-oral imaging system for 3-D imaging of teeth and other dental features without requiring the use of a special powder or application of some other temporary coating for the tooth surface. The system offers high resolution, in the 25-50 µm range in one embodiment.

Conventional fringe projection imaging uses a series of parallel lines extending in the same direction, with successive images obtained by incrementally shifting the position of the lines, wherein the shift is in the orthogonal direction. For the phase shifting fringe projection method, at least three images, shifted in this manner, are typically needed in order to provide sufficient information for calculating the three-dimensional information of the tooth or other small object. The relative positions of the fringes for these three projected images are shifted, with each image, by an orthogonal offset O that is one-third of the fringe period, as represented by the image sequence with fringe images 100a, 100b, and 100c in FIG. 13A. The parallel lines of the fringe pattern extend in a predominant direction D; offset O is in a direction that is orthogonal to predominant direction D.

Figure 13B:
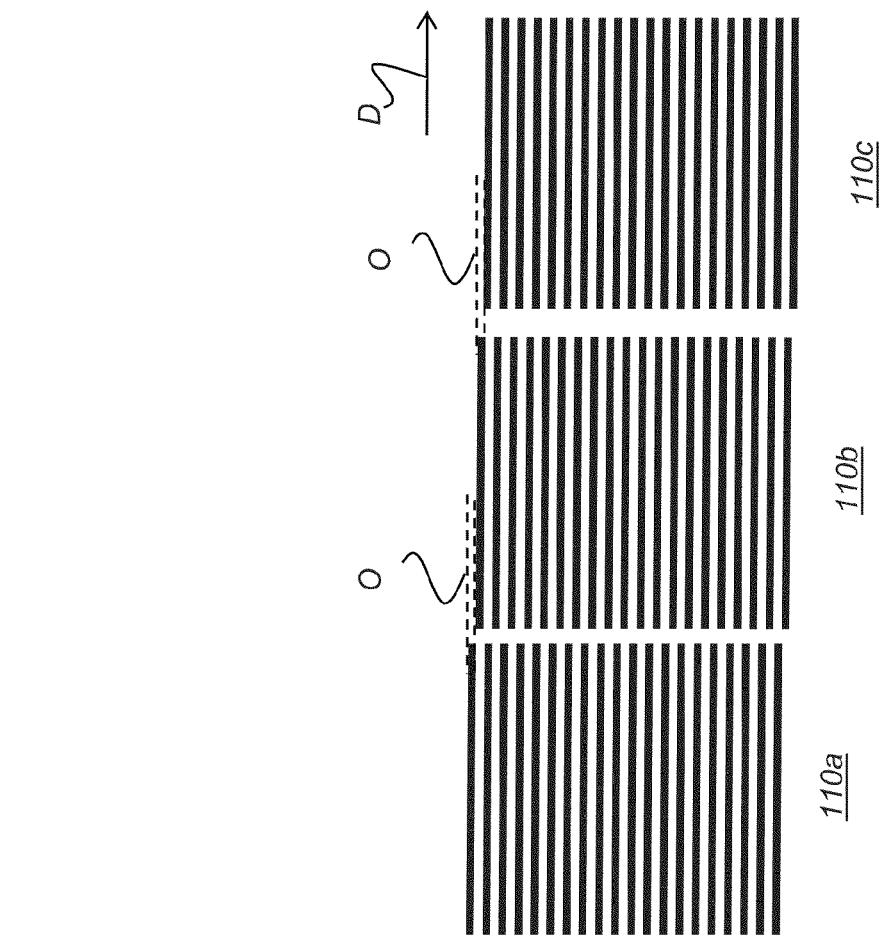
FIGS. 13A, 13B, and 13C show plan views of fringe patterns in sequences of images.
Figure 13A:
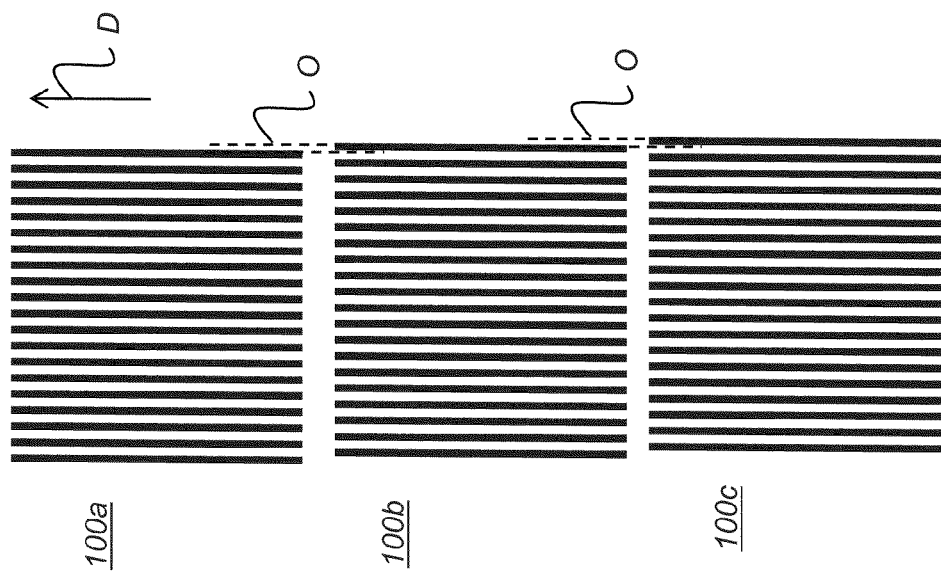
Figure 13C:
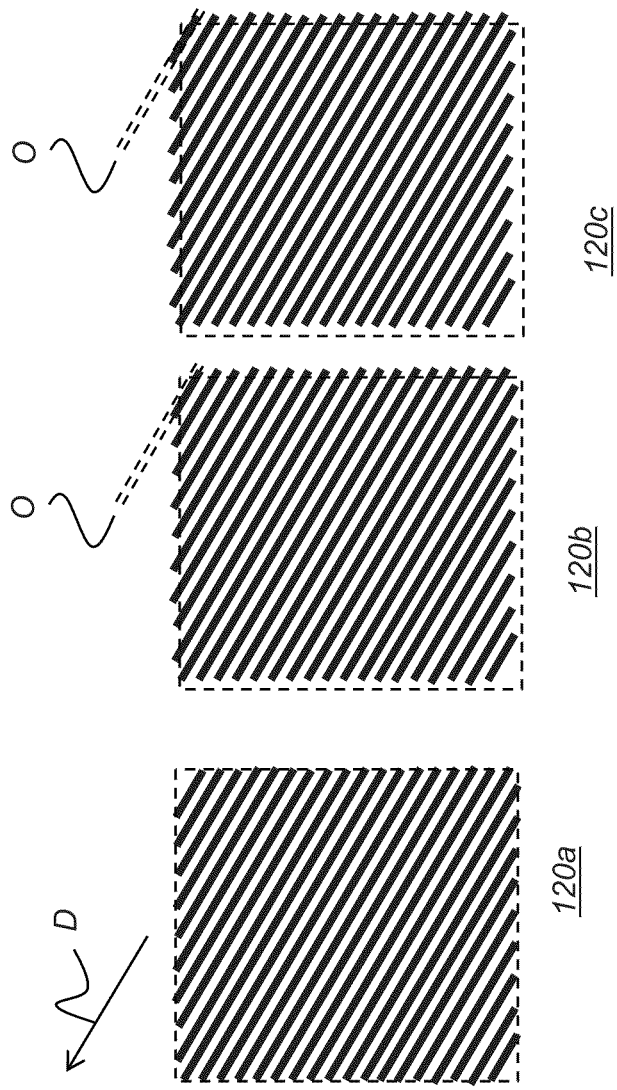

Because spatial light modulator 84 (FIG. 11) is used to generate the fringe pattern, the parallel lines can be oriented in any direction. FIG. 13B shows an orthogonal arrangement to that shown in FIG. 13A, with an image sequence that has fringe images 110a, 110b, and 110c and with offset O. In FIG. 13B, the predominant direction D is shifted substantially 90 degrees from the predominant direction of the FIG. 13A pattern. FIG. 13C shows an arrangement with the predominant direction D oriented at some other suitable angle, with fringe images 120a, 120b, and 120c and with offset O, again, with the offset O orthogonal to the predominant direction D of the extending line elements in the projected pattern.

The inventors have found the capability to change the angular orientation of the projected fringe pattern, along with shifting by an incremental offset O, to be helpful for improved detection of cracks and fracture lines in teeth. When the direction of the crack or fracture line extends in a direction that is orthogonal to the projected parallel lines, the problem may be difficult to detect. When the direction of the crack or fracture line extends in parallel, or at least substantially parallel to within no more than about 10 degrees from true parallel with respect to the projected lines, the problem is more readily detectable. The method of the present invention uses this pattern rotation capability to improve the visibility of cracks and fractures in tooth imaging.

Figure 14:
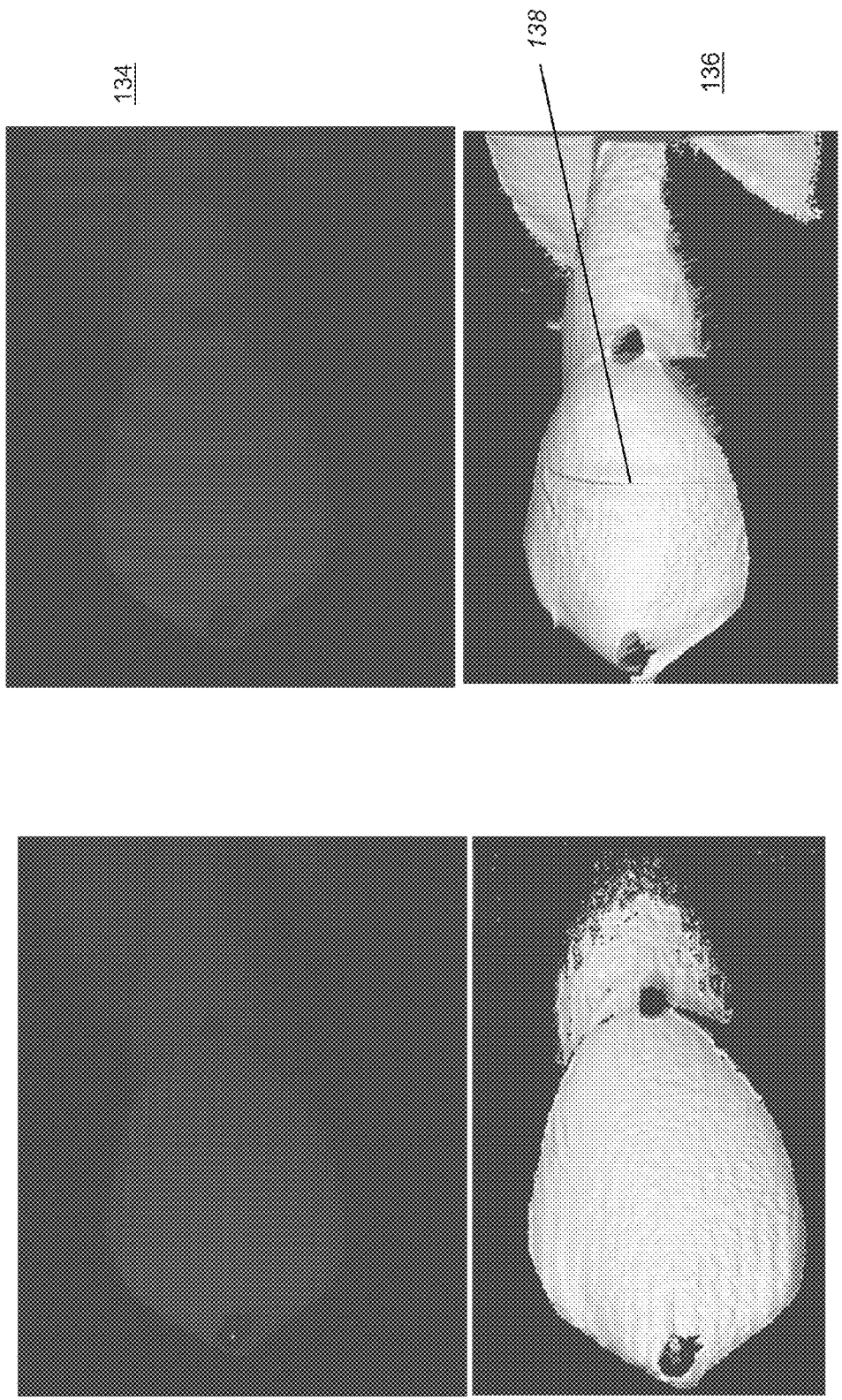
FIG. 14 shows exemplary images analyzed for cracks using an embodiment of the present invention.

In FIG. 14, the sequence of paired images 130 and 132 show the original fringe projection image 130 and processed image 132 for a tooth with a known crack. Because the lines in projection image 130 are orthogonal to the crack, visibility is very poor and the crack is very difficult to discern in processed image 132. The sequence of paired images 134 and 136 show, for the same tooth, how the use of projected lines at a variable angle in fringe projection image 134 improves detection of a crack 138. As noted with regard to the patterns in FIGS. 13A, 13B, and 13C, the patterns shown in fringe projection images 130 and 134 represent two orthogonal sets of fringe pattern images, with multiple images in each set, offset incrementally from each other. It must be emphasized that, although projection of the same pattern in orthogonal directions has a number of advantages for simplicity of processing, other arrangements are also workable, including a sequence that provides a first pattern oriented in a first direction followed by a second pattern that is oriented in a second direction that is shifted more than 10 degrees with respect to the first direction, but is not necessarily orthogonal.

Figure 15:
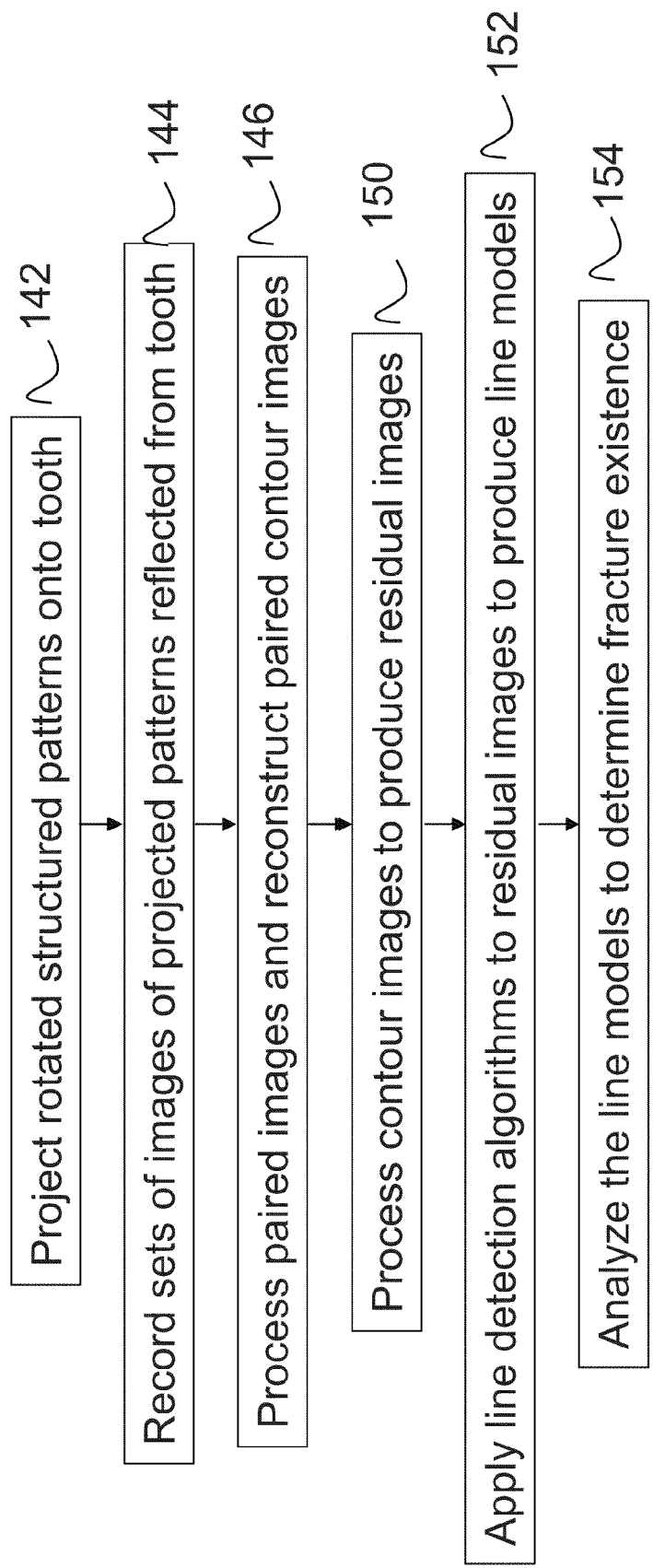
FIG. 15 is a logic flow diagram that shows a sequence of steps for identifying tooth cracks according to an embodiment of the present invention.

The logic flow diagram of FIG. 15 shows a sequence of steps used for detection of tooth fracture according to an embodiment of the present invention. In capture and acquisition steps 142 and 144, rotatable structured fringe patterns such as patterns 130 and 134 in FIG. 14 are projected on a tooth surface and are acquired by the imaging detector. Each projected pattern has a predominant direction, such as parallel lines extending in a first direction. A first set of at least two images is obtained for the projected pattern having a first direction; at least a second set is obtained for the pattern in a second direction, at an angle that is shifted by at least 10 degrees or more from the first set. According to an embodiment of the present invention, the second set is in a direction that is orthogonal with respect to the direction of the first set. In a processing step 146, each set of angularly shifted or orthogonally shifted sets of fringe pattern images is used to reconstruct a range image. A processing step 150 produces residual images, as described in more detail subsequently. A line model generation step 152 produces line models using the residual images. An analysis step 154 then analyzes the line models to detect a crack or other fracture line. Detailed exemplary steps of acquiring a pair of range images (or 3-D surface images) from a pair of orthogonal sets of fringe patterns are the following:

(i) setting a first rotatable fringe pattern at a first angle;

(ii) projecting and acquiring the first set of fringe patterns toward the tooth surface; each image in the first set is offset, in an offset direction, from the preceding image in the set;

(iii) setting a second rotatable fringe pattern at a second angle, such as substantially orthogonal to the first angle, but shifted by at least 10 degrees from the angular direction of the first set of fringe patterns;

(iv) projecting and acquiring the second set of fringe patterns toward the tooth surface; each subsequent image in the second set is also offset from the preceding image in the second set;

(v) reconstructing the surface using the sets of images from the first and second sets of fringe patterns.

The method of reconstructing a 3-D surface contour image, alternately termed a range image, is based on the phase shifting method described in the previous sections.

An automatic process of detecting the crack is elaborated. In processing step 150, the obtained fringe projection images are processed by de-noising filters, linear structure enhancing filters, and image registration processes.

The de-noising filter is used to smooth the images for subsequent procedures. One example of a known de-noising filter is proposed by Rudin, Osher and Fatemi in "Nonlinear Total Variation based noise removal algorithms", *Physica D* 60 259-268, 1992. Linear structure enhancing filters enable the enhancement of signals caused by cracks in the images and are also familiar to those skilled in image processing. One exemplary type of linear structure enhancing filter can be found in the article by Joachim Weickert entitled "Coherence-enhancing diffusion filtering", *International Journal of Computer Vision* 31(2/3), 1999, pp. 111-127.

A registration process is needed to align contour images of the two different sets for improved crack detection. In terms of image registration terminology, the two images involved in the registration process are referred as a source image and a reference image. With reference to FIG. 14, either one of images 132 or 136 can be considered a source image or a reference image. Denote the source image and the reference image by $I(x_t, y_t, t)$ and $I(x_{t+1}, y_{t+1}, t+1)$ respectively. The notations x and y are the horizontal and vertical coordinates of the image coordinate system, and t is the image index (image 1, image 2, etc.). The origin, (x=0, y=0), of the image coordinate system is defined at the center of the image plane. It should be pointed that the image coordinates, x and y, are not necessarily integers.

For convenience in implementation, the image (or image pixel) is also indexed as I(i, j) where i and j are strictly integers and parameter t is ignored for simplicity. This representation aligns with indexing a matrix in the discrete domain. If the image (matrix) has a height h and width w, the corresponding image plane coordinates, x and y, at location (i, j) can be computed as x=i−(w−1)/2.0, and y=(h−1)/2.0−j. The column index i runs from 0 to w−1. The row index j runs from 0 to h−1.

In general, the goal of the registration process is to find an optimal transformation function $\Phi_{t+1}(x_t, y_t)$ such that $$[x_{t+1}, y_{t+1}, 1]^T = \Phi_{t+1}(x_t, y_t)[x_t, y_t, 1]^T \quad (10\text{-}1)$$

The transformation function of Equation (10-1) is a 3×3 matrix with elements shown in Equation (10-2).

$$\Phi = \begin{bmatrix} \phi_{00} & \phi_{01} & \phi_{02} \\ \phi_{10} & \phi_{11} & \phi_{12} \\ 0 & 0 & 1 \end{bmatrix} \quad (10\text{-}2)$$

The transformation matrix consists of two parts, a rotation sub-matrix $$\begin{bmatrix} \phi_{00} & \phi_{01} \\ \phi_{10} & \phi_{11} \end{bmatrix}$$

and a translation vector $$\begin{bmatrix} \phi_{02} \\ \phi_{12} \end{bmatrix}.$$

Note that the transformation function $\Phi$ is either a global function or a local function. A global function $\Phi$ transforms every pixel in an image in a same way. A local function $\Phi$ transforms each pixel in an image differently based on the location of the pixel. For the task of image registration, the transformation function $\Phi$ could be a global function or a local function or a combination of the two.

In practice, the transformation function $\Phi$ generates two displacement maps, X(i, j), and Y(i, j), that contain the information that could bring pixels in the source image to new positions that align with the corresponding pixel positions in the reference image. In other words, the source image is to be spatially corrected and become a registered source image. For both displacement maps, X(i, j) and Y(i, j), the column index i runs from 0 to w−1 and the row index j runs from 0 to h−1.

Note that the registration algorithm used in computing the image transformation function $\Phi$ could be a rigid registration algorithm, a non-rigid registration algorithm or a combination of the two. Those skilled in the art can appreciate that there are numerous registration algorithms that can carry out the task of finding the transformation function $\Phi$ that generates the needed displacement maps for the correction of misalignment in two relevant images. Exemplary algorithms can be found in the Insight Segmentation and Registration Toolkit (ITK) from Kitware, Inc.

Also in step 150, a differencing operation is applied to this processed and aligned pair of contour or range images (such as 132 and 136 in FIG. 14) to produce a residual image (not shown). An exemplary differencing operation is subtracting one image from the other, thus generating a residual image.

As shown in the FIG. 15 sequence, a line model generation step 152 processes the residual image to produce a line model. The exemplary line structure detection algorithm used in one embodiment of the present invention is the RANSAC algorithm that is well known in the field of computer vision for applications such as solving correspondence problems and estimating the fundamental matrix for stereo vision ("Random Sample Consensus: A Paradigm for Model Fitting with Applications to Image Analysis and Automated Cartography", by Martin Fischler and Robert Bolles, *Graphics and Image Processing*, volume 24, number 6, 1981).

The RANSAC algorithm is an iterative method to estimate parameters of a mathematical line model from a set of observed data which contains outliers. It is a non-deterministic algorithm in the sense that it produces a reasonable result with a certain probability, with this probability increasing as more iterations are executed. The input to the RANSAC algorithm is a set of observed data values, a parameterized model which can explain or be fitted to the observations. RANSAC achieves its goal by iteratively selecting a random subset of the original data. These data are hypothetical inliers that belong to a set of points that constitute a line structure, and this hypothesis is then tested. In crack detection of the present invention, the original data are composed of non-zero value pixels in the residual image.

The RANSAC algorithm essentially is a two-step process. The algorithm first randomly picks s data points from the original data and uses the picked data point to instantiate a line model. It then determines the set of inliers as the data points lying within a distance threshold t of the line model. This two-step process repeats N times. The model that contains the largest set of inliers is selected as the final line model.

There are two parameters involved in the RANSAC algorithm: the distance threshold t and the number of trials, N. The distance threshold t determines the points that will be included in the set of inliers of a line model that is determined by s data points randomly selected from the original data. The distance threshold t is chosen empirically, e.g. 2 points. It is infeasible to try every possible combination of s data points from the original data, while N must be large enough to ensure a high probability of success of finding a line structure if there is one.

Let p be the desired probability of success, the computation of the number of trials, N, can be expressed as $$N = K(\varepsilon, p) = \frac{\log(1-p)}{\log(1-(1-\varepsilon)^s)}$$

where $\varepsilon$ is the proportion of erroneous data, $(1-\varepsilon)^s$ is the probability of picking a non erroneous data. Therefore (1−

$(1-\epsilon^s)^N$ is the probability of failure for all trials. Denote a data count by c. The parameter N can be chosen adaptively with the following algorithm.

---
Set $N \leftarrow \infty$ and $c \leftarrow 0$
White $N > c$ repeat
  1. randomly select s data points and instantiate the model from this subset
  2. Determine the set of inliers as the data lying within a distance threshold t of the model
  3. compute the proportion $\epsilon$ of outliers
  4. Set $N \leftarrow \min(N, K(\epsilon, p))$
  5. increment c by 1
Terminate

---

Applying the above RANSAC algorithm in step 152 to the residual image results in a line model that fits to the underlying line structure in the image. The parameters, angle $\phi$ and position vector o, of the resultant line model are used in analysis step 154 to analyze the line model to determine fracture existence.

The angle $\phi$ and position vector o are defined with respect to the local image coordinate system of the residual image. The position vector o is calculated using the s data points that generate the largest number of inliers in the RANSAC iterations. These two parameters, angle $\phi$ and position vector o, enable the computation of a peak-to-peak ratio, $\mathcal{R}$, of two orthogonal integral-curves. The following steps describe the procedure for computing the ratio $\mathcal{R}$.

Cropping band $B(\phi)$ contains W lines $l_k(\phi)$: $B(\phi) = l_k(\phi)$; $k \in [1, \ldots, W]$, and the center of line $l_k(\phi)$ is o. Denote a pixel on line $l_k(\phi)$ by $p_{l_k,i}(\phi)$. Line $l_k$ is a collection of pixels:
$l_k = \{\hat{I}(p_{l_k,i}(\phi))\}$, $i \in [-(L-1)/2, \ldots, (L-1)/2]$, L is the line length. Here, $\hat{I} = |\nabla I|$ is the gradient image of the residual image I. For notation simplicity, parameter $\phi$ is omitted in some of the expressions that follow. Denote the integral curve of the set of lines $\{l_k\}$ in the band by $s(\phi)$ with elements $s_i(\phi)$: $s(\phi) = \{s_i(\phi)\}$, where $$s_i = \frac{1}{W} \sum_{k=1}^{W} \hat{I}(p_{l_k, i}).$$

The pixel coordinate $p_{l_k, i}$ can be computed as: $p_{l_k, i} = i f_l + o_{l_k}$, where $$f_l = \begin{bmatrix} f_l^{x^1} \\ f_l^{x^2} \end{bmatrix} = \begin{bmatrix} \cos(\phi) \\ -\sin(\phi) \end{bmatrix}$$

and the centers $o_{l_k}$ are obtained through: $o_{l_k} = k f_b + o$; $k \in [-(W-1)/2, \ldots, (W-1)/2]$, and $$f_b = \begin{bmatrix} f_b^{x^1} \\ f_b^{x^2} \end{bmatrix} = \begin{bmatrix} \sin(\phi) \\ \cos(\phi) \end{bmatrix}.$$

With the same formulation, another integral computation can be made at an angle $\phi = \phi + 90°$ resulting in an integral curve $S(\phi)$. Peak-to-peak values are computed for these two curves. $p(\phi)$ for $s(\phi)$, $p(\phi)$ for $s(\phi)$. The ratio $\mathcal{R} = p(\phi)/p(\phi)$ is the feature to be used in step 154 to detect linear structures. If the ratio, $\mathcal{R}$, exceeds a predefined threshold, a crack or a fracture is reported.

The above described procedures, steps 142 through 154 in FIG. 15, are performed at a plurality of rotation angles for a plurality of paired orthogonal sets of fringe patterns. Therefore cracks can be automatically detected without human intervention. The detected cracks or fractures can be easily superimposed with the three dimensional tooth surface contour image for visualization. Additional highlighting can be added to show the identified crack.

Consistent with one embodiment, the present invention utilizes a computer program with stored instructions that perform on image data accessed from an electronic memory, to provide tooth crack detection and display in accordance with the method described. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including networked processors. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for imaging the surface of a tooth comprising:
   a computer, at least in part, for executing the method;
   recording a first set of 2-D images of the tooth, wherein each image in the first set of images is illuminated according to a fringe pattern generator oriented in a first direction;
   recording a subsequent different second set of 2-D images of the tooth, wherein each image in the second set of images is illuminated according to a fringe pattern generator oriented in a second direction that is shifted more than 10 degrees with respect to the first direction;
   reconstructing a first 3-D contour image according to the recorded first set of images and a second 3-D contour image according to the recorded second set of images;
   forming a 3-D residual image as a subtraction operation between the first and second 3-D contour images; and
   analyzing the 3-D residual image;
   detecting a crack on the tooth by applying a line model algorithm; and
   displaying surface conditions of the tooth.

2. The method of claim 1 wherein detecting the crack comprises applying a line structure detection algorithm.

3. The method of claim 1 wherein detecting the crack comprises applying an iterative line model algorithm.

4. A method for imaging the surface of a tooth comprising:
   a computer, at least in part, for executing the method;
   projecting and recording a first set of images of the tooth, wherein each image in the first set of images is illuminated according to a pattern generator oriented in a first direction;
   subsequently projecting and recording a second separate set of images of the tooth, wherein each image in the second set of images is illuminated according to a pattern generator oriented in a second direction that is orthogonal to the first direction, where the second separate set of images of the tooth are different from the first set of images;
   reconstructing a first 3D contour image according to the recorded first set of images and a second 3D contour image according to the recorded second set of images;
   forming a residual 3D image as a subtraction between the first and second 3D contour images;
analyzing the residual 3D image; and
   detecting a crack in the tooth surface by applying a line model algorithm to the residual image; and
displaying surface conditions of the tooth.

5. The method of claim 4 wherein detecting the crack comprises applying a line structure detection algorithm.

6. The method of claim 4 wherein detecting the crack comprises applying an iterative line model algorithm.

7. A system for imaging a surface of a tooth, the system comprising:
   one or more memory devices storing instructions; and
   one or more processors configured to execute the instructions to perform a method comprising:
   recording a first set of 2D images of the tooth, wherein each 2D image in the first set of 2D images is illuminated according to a first fringe pattern generator oriented in a first direction;
   recording a subsequent separate second set of 2D images of the tooth, wherein each 2D image in the second set of 2D images is illuminated according to a second fringe pattern generator oriented in a second direction that is shifted more than 10 degrees with respect to the first direction;
   reconstructing a first contour image according to the recorded first set of images and a second contour image according to the recorded second set of images;
   forming a residual image as a subtraction operation between the first and second contour images;
   analyzing the residual image; and
   detecting a crack in the tooth surface by applying a line model algorithm to the residual image; and
   displaying surface conditions of the tooth.

8. The system of claim 7, the system further comprising:
   a light source; and
   a spatial light modulator for receiving light from the light source, forming a first fringe pattern oriented in a first direction, and forming a second fringe pattern oriented in the second direction.

9. The system of claim 7, wherein forming the residual image comprises obtaining the difference between the first and second contour images, where the first and second contour images are 3D contour images.

10. The system of claim 7, wherein detecting the crack comprises applying a line structure detection algorithm.

11. The system of claim 7, wherein detecting the crack comprises applying an iterative line model algorithm, where the first fringe pattern is the same as the second fringe pattern.

12. The system of claim 7, wherein forming the residual image comprises obtaining the difference between the first contour image, the second contour image and a plurality of additional contour images, where the plurality of additional contour images are 3D contour images, where the plurality of additional contour images are formed by recording a subsequent separate sets of 2D images of the tooth, wherein each 2D image in the second set of 2D images is illuminated according to an additional fringe pattern oriented in a direction that is shifted more than 10 degrees with respect to the direction of the fringe pattern of the previous separate set of 2D images of the tooth.

* * * * *